United States Patent
Kaczanowski et al.

(10) Patent No.: US 9,492,579 B2
(45) Date of Patent: Nov. 15, 2016

(54) PSYLLIUM FUMIGATED WITH METHYL BROMIDE

(71) Applicant: The Procter & Gamble Company, Cincinnati, OH (US)

(72) Inventors: Matthew John Kaczanowski, Cincinnati, OH (US); Stephen Richard Cammarn, Mason, OH (US); Rohan Lalith Wimalasena, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 419 days.

(21) Appl. No.: 14/059,501

(22) Filed: Oct. 22, 2013

(65) Prior Publication Data

US 2015/0110673 A1 Apr. 23, 2015

(51) Int. Cl.
*A61L 2/20* (2006.01)
*A01N 29/00* (2006.01)

(52) U.S. Cl.
CPC *A61L 2/20* (2013.01); *A01N 29/00* (2013.01)

(58) Field of Classification Search
CPC .............................. A61L 12/20; A01N 29/00
See application file for complete search history.

(56) References Cited

U.S. PATENT DOCUMENTS 4,911,889 A * 3/1990 Leland ................... A23B 9/025
422/26
5,678,352 A * 10/1997 Leitner ............... A01M 13/003
43/124
6,203,824 B1 3/2001 Banks et al.

OTHER PUBLICATIONS

Dudley et al. "Methyl Bromide as a Fumigant for Foods." Food Research (1941) 7 421-429.*
Zettler et al. "Chemical control of stored product insects with fumigants and residual treatments." Crop Protection 19 (2000) 577-582.*
PCT International Search Report dated Jan. 29, 2014—4 pages.
R. H. Thompson, "A Review of the Properties and Usage of Methyl Bromide as a Fumigant", J. Stored Prod. Res., vol. 1, pp. 353-376, 1966.
Reeves et al., "Organic and Inorganic Bromide Residues in Spices Fumigated with Methyl Bromide", J. Agric. Food Chem., vol. 33, pp. 780-783, 1985.
Urvesh Psyllium Industries Limited—retrieved from the Internet on Jan. 28, 2016—http://www.urvesh.com/products_psyllium_husks.html (first published as http://www.urvesh.com/htms/ph95.htm).

* cited by examiner

*Primary Examiner* — Timothy Cleveland
(74) *Attorney, Agent, or Firm* — Alexandra S. Anoff

(57) ABSTRACT

A method for fumigating psyllium husk. The method comprises filling a fumigation chamber with psyllium husk chamber is at least 35% filled with bags of psyllium husk, fumigating the psyllium husk with at least 40 g/m$^3$ of methyl bromide for at least 24 hours, and degassing the chamber for at least 6 hours to form fumigated psyllium husk. The fumigated psyllium husk comprises less than 50 ppm inorganic bromide residue and the fumigated psyllium husk does not comprise an insect infestation or a khapra beetle infestation.

10 Claims, 7 Drawing Sheets

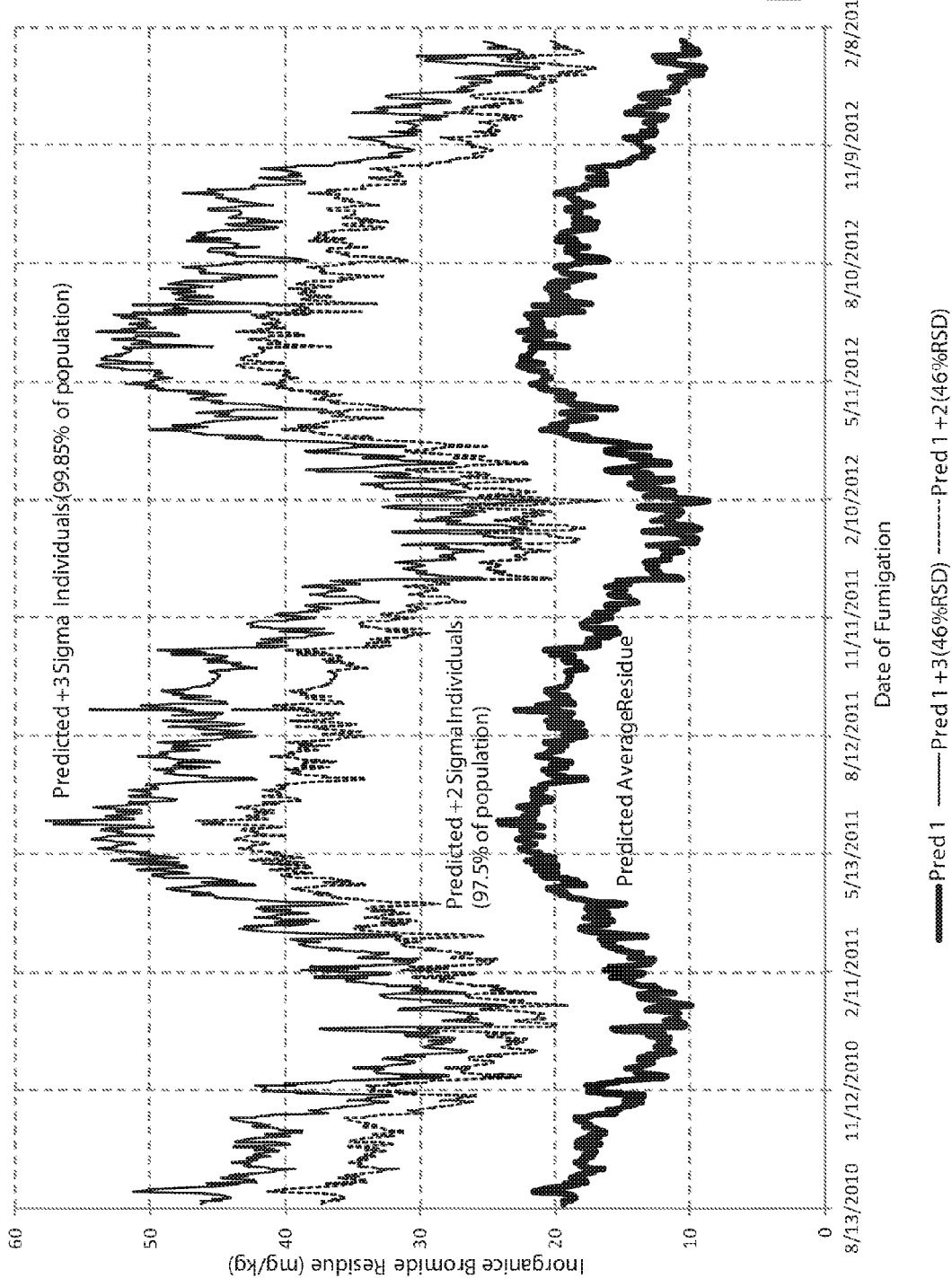

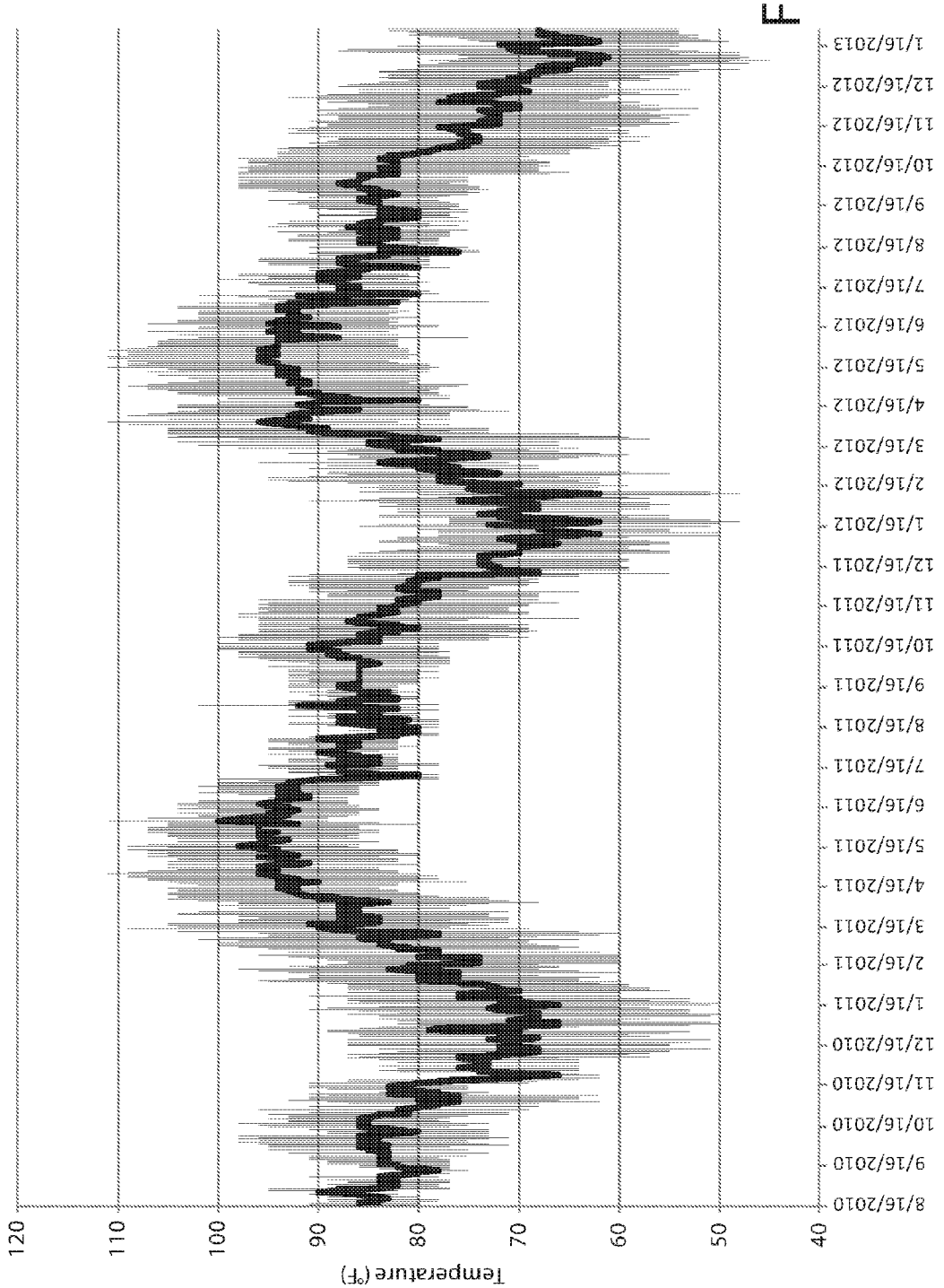

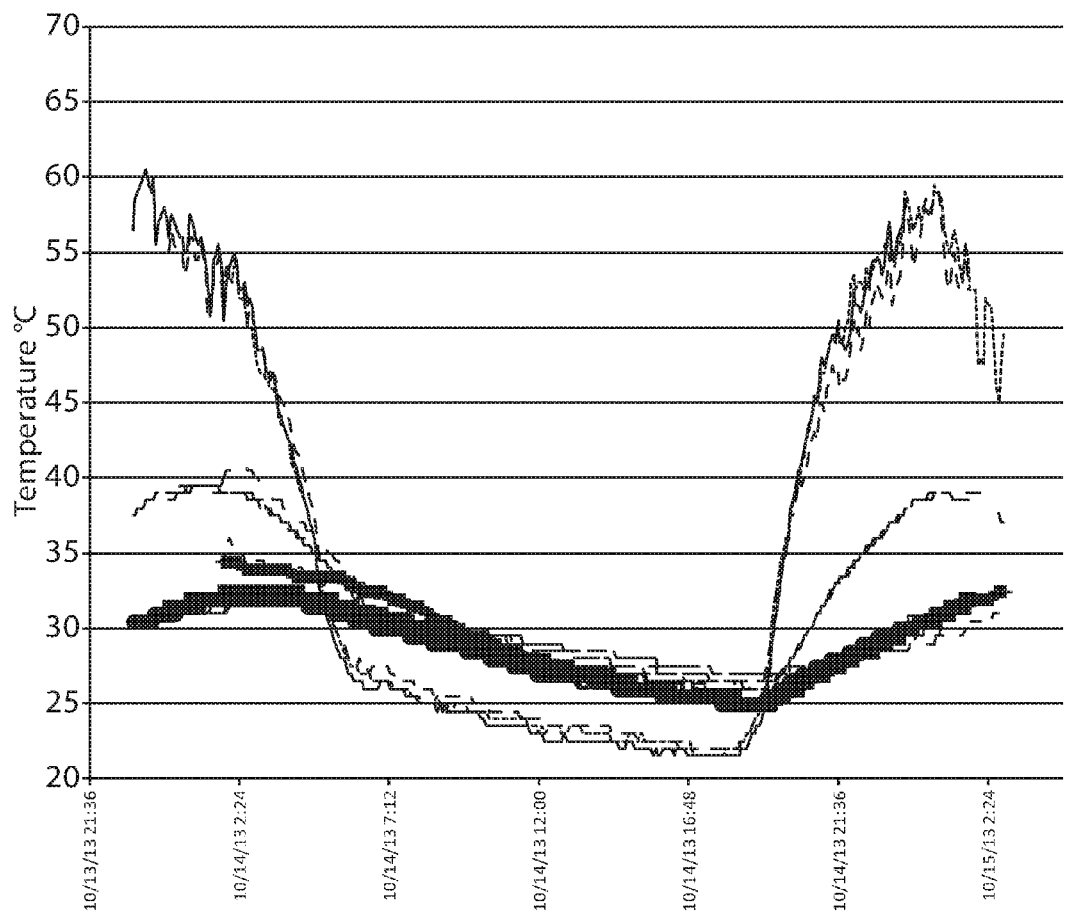
Fig. 4B
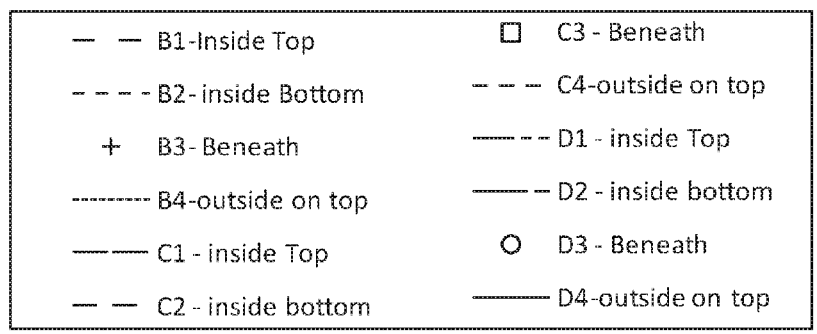

US 9,492,579 B2

PSYLLIUM FUMIGATED WITH METHYL BROMIDE

CROSS REFERENCE TO RELATED APPLICATION

This application claims the benefit of U.S. Provisional Application No. 61/716,710 filed Oct. 22, 2012.

FIELD OF THE INVENTION

The present invention is generally related to a method for producing a fumigated psyllium husk product with less than about 50 ppm inorganic bromide residue.

BACKGROUND OF THE INVENTION

Agriculture products are often fumigated to control pests, including insects, plant pathogens, weeds, mollusks, nematodes, vertebras, and microbes that can destroy property, cause nuisance, spread disease or are vectors for disease.

Psyllium and other grains are often fumigated with methyl bromide, which is an effective fumigant since it is highly toxic to most pests. However, methyl bromide can create residual inorganic bromide in the fumigated products. USP <561> has established that 50 ppm is the maximum amount of inorganic bromide residue that can be in or on grains, such as psyllium.

When processing psyllium, including psyllium husk, it can be difficult to fumigate with enough methyl bromide that the pests, especially the khapra beetle and other insects, are destroyed while maintaining a level of inorganic bromide residue that is less than 50 ppm. The USDA recommends treating grains not for propagation with a minimum of 40 g/m$^3$ of methyl bromide at 21° C. or greater. However, when this level is used with psyllium the fumigation can result in inorganic bromide residue that is greater than 50 ppm, which results in psyllium that does not meet compendia and must be discarded.

There is a need for an effective method to fumigate psyllium, including psyllium husk, with methyl bromide where the fumigated psyllium comprises less than 50 ppm inorganic bromide residue.

SUMMARY OF THE INVENTION

A method for fumigating psyllium comprising: (a) filling a fumigation chamber with psyllium husk such that the chamber is at least 35% filled by volume with bags of psyllium husk; (b) fumigating the psyllium husk with at least about 40 g/m$^3$ of methyl bromide for at least 24 hours; (c) degassing the chamber for at least about 6 hours to form fumigated psyllium husk; wherein the fumigated psyllium husk comprises less than about 50 ppm inorganic bromide residue and wherein the fumigated psyllium husk does not comprise an insect infestation and the fumigated psyllium husk does not comprise a khapra beetle infestation.

A method for fumigating psyllium husk comprising: (a) filling a shipping container with psyllium husk such that the shipping container comprises from about 40 kg to about 100 kg psyllium husk per m$^3$ of the shipping container; (b) fumigating the psyllium husk with about 30 g/m$^3$ to about 70 g/m$^3$ of methyl bromide for about 12 hours to about 36 hours; (c) degassing the chamber for at least 4 hours to form fumigated psyllium husk; wherein the fumigated psyllium husk comprises less than about 50 ppm inorganic bromide residue and wherein the psyllium husk does not comprise an insect infestation and the fumigated psyllium husk does not comprise a khapra beetle infestation and wherein the psyllium husk is stored in one or more bags.

A method for providing fumigated and sanitized psyllium husk comprising: (a) filling a fumigation chamber with psyllium husk such that the chamber comprises about 35% to about 50% psyllium husk by volume; (b) fumigating the psyllium husk with at least about 40 g/m$^3$ of methyl bromide for at least about 24 hours; (c) degassing the chamber for at least about 6 hours to form fumigated psyllium husk; (d) steam sanitizing the psyllium husk; wherein the fumigation is performed at a temperature that is less than or equal to about 40° C.; wherein the fumigated psyllium husk comprises less than about 50 ppm inorganic bromide residue and wherein the fumigated psyllium husk does not comprise an insect infestation and the fumigated psyllium husk does not comprise a khapra beetle infestation.

BRIEF DESCRIPTION OF THE DRAWINGS

FIG. 3A shows the predicted residual inorganic bromide from August 2010 to January 2013, based on the average daily temperature in Ahmedabad, India in FIG. 3B;

FIG. 3B shows the daily temperature including the average daily temperature in Ahmedabad, India from August 2010 to January 2013;

FIG. 4B shows the temperature profile over time for a sheltered shipping container during fumigation and off gassing.

DETAILED DESCRIPTION OF THE INVENTION

Figure 1:
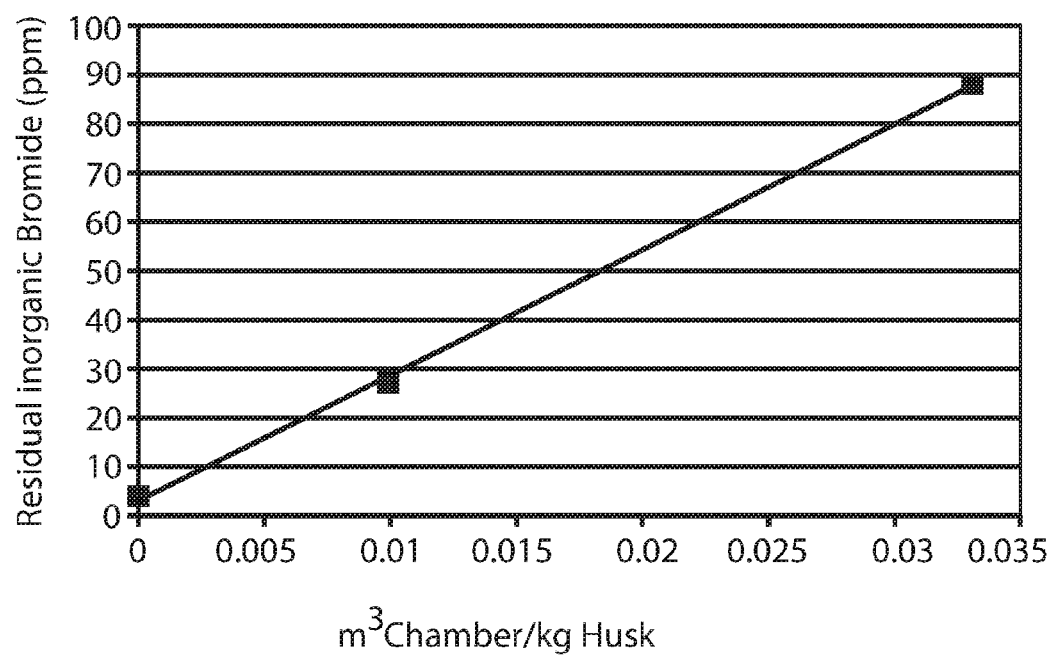
FIG. 1 shows the residual inorganic bromide over the mass of psyllium husk in the chamber when the psyllium husk was placed in a jute bag.

The present invention relates to a method of fumigating psyllium where the fumigated psyllium comprises less than about 50 ppm inorganic bromide residue and is substantially free of pests. The method involves fumigating psyllium husk in bags made of natural fiber, for example jute bags. The bags are placed in a fumigation chamber so the fumigation chamber comprises at least about 50 kg psyllium husk per m$^3$ of the chamber. In one example, the fumigation chamber is a shipping container. Current methods can use too few bags of psyllium husk in the chamber and the levels of inorganic bromide in or on the finished product can be above 50 ppm. However, if too many bags of psyllium husk are loaded into the fumigation chamber then, the chamber is too full and the methyl bromide cannot circulate properly and destroy the pests. The psyllium husk is treated with about 40 g/m$^3$ of methyl bromide for a suitable amount of time, such as, for example, about 24 hours, and then the chamber is degassed for a suitable amount of time, such as, for example, about 6 hours. Surprisingly, psyllium husk that is fumigated using the present invention does not have an insect or khapra beetle infestation.

In one example, the psyllium husk can only be fumigated with methyl bromide one time. In one example, other means can be used for further pest control and/or sanitation. In one example, after the psyllium husk is fumigated it is steam sanitized.

In one example, the fumigated product comprises less than about 50 ppm inorganic bromide residue, in another example less than about 45 ppm inorganic bromide residue, in another example less than about 40 ppm inorganic bromide residue, in another example less than about 35 ppm inorganic bromide residue, in another example less than about 30 ppm inorganic bromide residue, in another example less than about 25 ppm inorganic bromide residue, in another example less than about 15 ppm inorganic bromide residue, in another example less than about 10 ppm inorganic bromide residue, and in another example less than about 5 ppm inorganic bromide residue.

In one example, the psyllium husk is treated with about 20 to about 100 $g/m^3$ of methyl bromide, in another example about 25 to about 80 $g/m^3$ of methyl bromide, in another example about 30 to about 70 $g/m^3$ of methyl bromide, in another example about 35 to about 50 $g/m^3$ of methyl bromide, and in another example about 38 to about 45 $g/m^3$ of methyl bromide. In one example, the psyllium husk is treated with about 40 $g/m^3$ of methyl bromide.

In one example, the density of the psyllium husk in the fumigation chamber comprises about 25 to about 150 kg psyllium husk per $m^3$ of chamber, in another example about 35 to about 125 kg psyllium husk per $m^3$ of chamber, in another example about 40 to about 100 kg psyllium husk per $m^3$ of chamber, in another example about 45 to about 75 kg psyllium husk per $m^3$ of chamber, about 50 to about 70 kg psyllium husk per $m^3$ of chamber, another example about 53 to about 57 kg psyllium husk per $m^3$ of chamber, and in one example about 55 to about 56 kg psyllium husk per $m^3$ of chamber.

In another example, the fumigation chamber is loaded so it contains about 20% to about 80% psyllium husk by volume, in another example about 25% to about 75% psyllium husk by volume, in another example about 30% to about 65% psyllium husk by volume, in another example about 33% to about 55% psyllium husk by volume, in another example about 35% to about 50% psyllium husk by volume, in another example about 38% to about 45% psyllium husk by volume, and in another example about 40% to about 44% psyllium husk by volume. In one example, the chamber comprises about 42% psyllium husk by volume.

In another example, once the fumigation chamber is loaded with psyllium husk it comprises about 20% to about 80% empty space, in another example about 25% to about 75% empty space by volume, in another example about 35% to about 70% empty space by volume, in another example about 45% to about 77% empty space by volume, in another example about 50% to about 65% empty space by volume, in another example about 55% to about 62% empty space by volume, in another example about 56% to about 60% empty space by volume. In one example, the chamber comprises about 58% empty space by volume. Empty space can include air but does not include psyllium, including psyllium husk, in bags.

The fumigation chamber can be filled with any suitable mass of psyllium husk and the mass can depend on the size of the chamber. In one example, the chamber is loaded with about 5000 kg to about 15,000 kg psyllium husk, in another example about 7000 kg to about 12,000 kg psyllium husk, in another example about 8500 kg to about 10,500 kg psyllium husk, and in another example about 9000 kg to about 10,000 kg psyllium husk. In one example, the chamber is loaded with about 9500 kg psyllium husk. In another example, the chamber is loaded with about 15,000 kg to about 25,000 kg psyllium husk, in another example about 16,000 kg to about 22,000 kg, in another example about 17,000 kg to about 21,000 kg, and in another example about 18,000 kg to about 20,000 kg. In one example, the chamber is loaded with 19,000 kg of psyllium husk.

The fumigation chamber can be any volume. In one example, the volume of the chamber can be from about 50 to about 300 $m^3$, in another example about 75 to about 275 $m^3$, in another example about 150 to about 250 $m^3$, and in another example about 200 $m^3$ to about 230 $m^3$. The chamber can be any height. In one example, the chamber is about 1 to about 5 m tall, in another example about 2 to about 4 m tall, and in another example the chamber is about 3 m tall.

The bags filled with psyllium husk can be made out of any suitable material. In one example, the bags are made out of jute. In another example, the bags are made out of a natural fiber. In one example, the bags are made out of any breathable material. In another example, the bags are made out of cloth, canvas, cotton, or combinations thereof. In another example, the bags are made out of a synthetic material.

The bags filled with psyllium husk can be any suitable size. In one example the bags can be from about 20 kg to about 100 kg, in another example about 25 kg to about 80 kg, in another example about 30 kg to about 78 kg, in another example about 33 kg to about 75 kg, in another example about 35 kg to about 65 kg, and in another example about 37 kg to about 50 kg. In one example, the bag is about 38 kg. In another example the bag is about 75 kg.

The method for producing a fumigated psyllium product, including fumigated psyllium husk, with less than about 50 ppm inorganic bromide residue can be performed as follows:

First, the psyllium husk can be separated from the psyllium seed. The psyllium seed can be discarded and only the psyllium husk is fumigated. While not willing to be bound by theory, it is believed that psyllium seed absorbs too much methyl bromide which degrades to inorganic bromide reside. Therefore, if the psyllium husk and seed are fumigated together and then separated, the psyllium husk can comprise more than about 50 ppm inorganic bromide residue.

The psyllium husk can comprise small amounts of psyllium seed and/or other organic components. In one example the psyllium husk comprises at least about 90% husk, in another example the psyllium husk comprises at least about 93% husk, in another example at least about 95% husk, in another example at least about 97% husk, and in another example at least about 99% husk.

The psyllium husk can then be fumigated. The psyllium husk can be packaged in jute bags. While not willing to be bound by theory, it is believed that jute bags reduce the level of inorganic bromide residue in or on the fumigated psyllium husk because jute bags are more permeable than polyethylene bags. The psyllium husk can be placed in any bag that has a similar permeability to jute.

Before fumigation begins the fumigation chamber can be cleaned and a tarpaulin sheet can be placed on the floor. The tarpaulin sheet can be any material. Non-limiting examples of materials for tarpaulin sheets can include cloth such as canvas, polyester, polyethylene, and combinations thereof. In one example, the tauplin sheet is made from plastic.

Next, the empty room volume can be calculated and then methyl bromide dosages can be calculated. The methyl bromide dosages are calculated so the air in the fumigation chamber comprises approximately 34,500 ppm of methyl bromide with an air density of 1210 $g/m^3$ at sea level. The recommended methyl bromide dosages for fumigating psyllium husk in jute bags can be found in Table 1 below.

TABLE 1

| Temperature | Concentration |
|---|---|
| ≥21° C. | 40 g/m$^3$ |
| 16° C.-20° C. | 48 g/m$^3$ |
| 11° C.-15° C. | 56 g/m$^3$ |

Surprisingly, it has been found that one factor that impacts the amount of inorganic bromide residue can be the ambient air temperature. If the temperature is too high, then the fumigation should not be performed because the level of inorganic bromide in some lots could be too high and there is a possibility that too many lots of fumigated psyllium husk would have to be discarded. In one example, the psyllium husk fumigation occurs at a temperature of less than or equal to about 30° C., in another example less than or equal to about 33° C., in another example less than or equal to about 35° C., in another example less than or equal to about 38° C., in another example less than or equal to about 40° C., in another example less than or equal to about 43° C., and in another example less than or equal to about 45° C. In another example, the psyllium husk fumigation occurs at a temperature greater than about 4.4° C., in another example greater than about 11° C.

Next, the jute bags filled with psyllium husk can be placed in the fumigation chamber. The jute bags can be placed in a way that allows good air circulation. If there is not good air circulation then the psyllium husk may not get properly fumigated and there could be pests in the fumigated product. However, if too few bags are loaded into the chamber then the psyllium husk can be exposed to too much methyl bromide and the fumigated product can comprise more than about 50 ppm inorganic bromide residue.

The jute bags filled with psyllium husk can be exposed to the methyl bromide gas for fumigation for an exposure period. If the psyllium husk is not fumigated for long enough then all of the pests, including larva and eggs, may not be destroyed. However, if the psyllium husk is fumigated for too long, then the levels of inorganic bromide that is in or on the fumigated psyllium husk can be too high. In one example, the exposure period can be for about 12 hours to about 36 hours, in another example from about 16 hours to about 32 hours, in another example about 18 hours to about 30 hours, in another example about 20 hours to about 28 hours, in another example about 22 hours to about 26 hours, and in another example about 23 hours to about 25 hours. In one example, the exposure period can be for about 24 hours.

After the fumigation is complete, jute bags are left in the chamber for off gassing by any suitable method including opening the door, flushing with fresh air, and/or using fans to exhaust the chamber. In one example, the jute bags are off gassed for at least about 4 hours, in another example for at least about 5 hours, in another example for at least about 6 hours, in another example for at least about 8 hours, in another example for at least about 10 hours, and in another example at least about 12 hours. In one example, the jute bags are off gassed for about 6 hours. In another example, you can off gas until the chamber has about 5 ppm or less.

In one example, the psyllium husk can be fumigated one time with methyl bromide. If the psyllium husk is placed in another container after fumigation, the other container can be fumigated separately. The jute bags of fumigated psyllium husk can be placed in large containers for shipping (hereinafter "shipping container"). In one example, the shipping container can be fumigated with methyl bromide before putting the fumigated psyllium husk inside. In another example, the shipping container can be the fumigation chamber and the psyllium husk can be fumigated inside the shipping container and then shipped without being transferred to another container. Fumigating in the shipping container can be advantageous because it prevents pests from entering the fumigated psyllium husk before it is put in the shipping container.

Any suitable shipping container can be used. In one example, the shipping container can be sealed, such as a standard shipping container or a refrigerated container (also referred to as a porthole container or an insulated container). In another example, the shipping container can be ventilated, which can help reduce moisture and/or humidity within the container. Non-limiting examples of ventilated shipping containers can include passively ventilated containers (also known as coffee containers), refrigerated containers, and open containers. If an open container is used it can be covered with a covering, such as a tarpaulin, to protect the cargo.

It has been found that the shipping container can be significantly warmer than the ambient temperature. For instance, if the ambient temperature is about 25° C., the air temperature inside a brown-painted steel shipping container rises to approximately 50° C., however if the same steel shipping container is painted white, the temperature only rises to about 38° C. In one example, the shipping container can be painted a light color, such as white, in order to reduce the temperature inside the shipping container.

In one example, to help control the internal temperature of the fumigation chamber, the fumigation chamber can be sheltered from the sun. In one example, a roof, that can be to a car port, can be built to shield the fumigation chamber from the sun, thereby reducing the ambient temperature within the fumigation chamber. In one example, the fumigation chamber is a shipping container and the shipping container can be painted a light color and/or sheltered from the sun.

The inorganic bromide residue can be measured using the method described in Bromine Containing Fumigants Determined as Total Inorganic Bromide published by the Community Reference Laboratory for Single Residue Methods, CVUA Stuttgart, Schaflandstr. 3/2, 70736 Fellbach, Germany (Nov. 11, 2008).

During storage, the pest population can be monitored regularly. Any suitable manner, including visual inspection or the USP Psyllium Husk Monograph, can be used to make sure that the psyllium husk is substantially free of pests. Visual inspection can include monitoring the pest population daily by monitoring the outside of the jute bags or the exterior of the super sacks, which are 950 kg weave bags that hold multiple jute bags, for signs of insects or visual inspection can include taking 200 g to 500 g of psyllium husk from the bags and checking to see if there are insects.

Substantially free of pests can mean that there is not an insect infestation according to the USP Psyllium Husk Monograph which defines an insect infestation as not more than 400 insect fragments, including mites and psocids per 25 g of powdered psyllium husk or not more than 100 insect fragments, including mites and psocids per 25 g of psyllium husk. If there is an insect infestation, the fumigated psyllium husk fails the Insect Infestation Test and cannot be shipped to the United States and is discarded. The term "insect infestation" as used herein shall be defined as using the definition provided by the USP Psyllium Husk Monograph as disclosed.

The psyllium husk can also be substantially free of the khapra beetle, which means that no living khapra beetle insects, larva, or eggs are found by using visual inspection. Fumigated psyllium husk that contains evidence of living khapra beetles cannot be shipped into the United States and are discarded.

Example 1

FIG. 1 shows the residual inorganic bromide over the specific volume in the chamber when the psyllium husk was placed in a jute bag. The psyllium husk was loaded into jute bags and placed in a chamber with a fixed volume. The amount of psyllium husk that was loaded into the chamber was varied. The psyllium husk was fumigated with methyl bromide at a concentration of 40 ppm for 24 hours. Following fumigation, the chamber was degassed for 6 hours. After 1-2 weeks, the inorganic bromide was measured and recorded. FIG. 1 shows that as more psyllium husk is loaded into the chamber, there is less residual inorganic bromide on the fumigated psyllium husk.

Example 2

Figure 2:
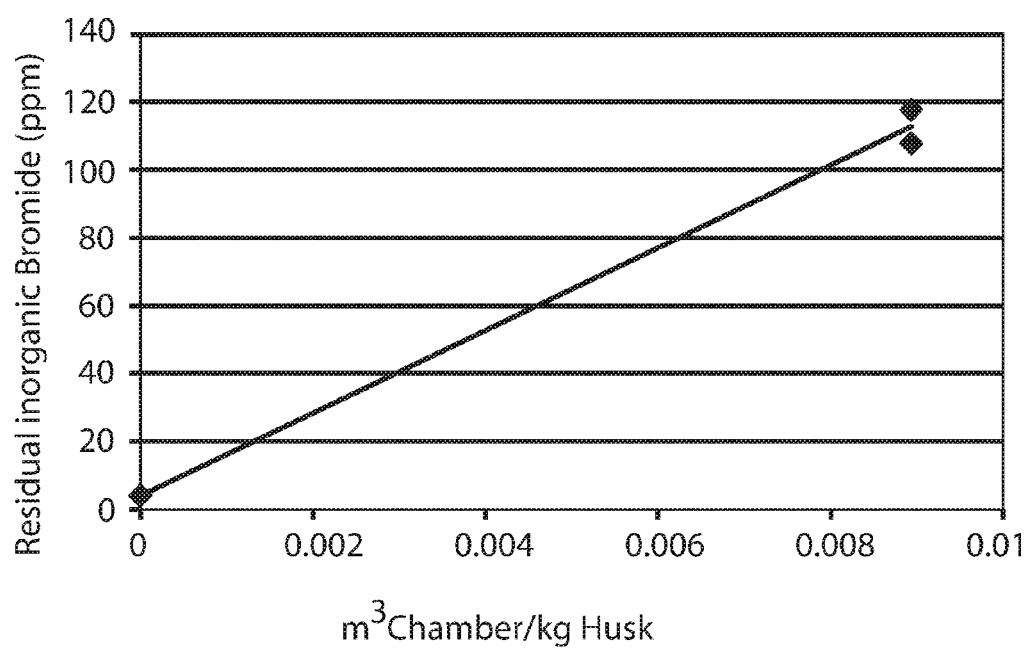
FIG. 2 shows the residual inorganic bromide over the mass of psyllium husk in the chamber when the psyllium husk was placed in a polypropylene bag.

FIG. 2 shows the residual inorganic bromide over the specific volume in the chamber when the psyllium husk was placed in a polypropylene bag. The polypropylene bag, of Example 2, is less permeable than the jute bag of Example 1. The chamber volume in Example 2 was fixed and was one third smaller than the chamber volume in Example 1. The psyllium husk was fumigated with methyl bromide at a concentration of 40 ppm for 24 hours. Following fumigation, the chamber was degassed for 6 hours. After 1-2 weeks, the inorganic bromide was measured and recorded. Again, FIG. 2 shows that as more psyllium husk is loaded into the chamber, there is less residual inorganic bromide. However, as compared to FIG. 1 in Example 1, more residual inorganic bromide was present when using the polypropylene bag. While not wishing to be bound by theory, it is believed that the less permeable bags trap the methyl bromide during degassing resulting in a higher concentration of inorganic bromide in or on the fumigated psyllium husk and in order to have a fumigated product with less than 50 ppm inorganic bromide, the fumigation chamber would have to be tightly packed which could decrease the air flow and resulting in pests in the fumigated product.

Example 3

FIG. 3A shows the predicted average residual inorganic bromide level on psyllium husk and the predicted residual bromide level within two and three standard deviations between August 2010 and January 2013, if the method described herein was performed in Ahmedabad, India. The model was created using the temperature information from FIG. 3B, which shows the daily temperature in Ahmedabad, India from August 2010 to January 2013. In FIG. 3B, the thick line in the center shows the average daily temperature and the high and the low temperature are represented by the thinner lines that are vertical on the chart.

FIG. 3A shows that heat is an important contributing factor for the amount of residual inorganic bromide and the warmer the temperature, the more residual inorganic bromide is on the psyllium husk. It can be costly and detrimental to the supply chain if psyllium husk has to be discarded because the residual inorganic bromide level is above the accepted amount, which is currently 50 ppm. Therefore, in order to be within three standard deviations, which means that the predicted failure rate is less than or equal to about 1.5 failures per 1000 lots, the psyllium husk must be fumigated at less than about 35° C. (95° F.). In order to be within two standard deviations, which means that the predicted failure rate is less than or equal to about 2.5 failures per 100 lots, the psyllium husk must be fumigated at less than about 40° C. (104° F.).

The current guidance states that the methyl bromide dosages for fumigation should decrease as the air temperature increases. The current guidance states that at temperatures greater than or equal to 21° C., 40 g/m$^3$ of fumigant should be used (see Table 1 herein) and the guidance includes no upper limit. However, based on the model herein, if the temperatures get too high, the psyllium husk should not be fumigated because there is a chance that the residual bromide residue will be at an unacceptable level. This is especially relevant, because psyllium is frequently grown and fumigated in India, where it can get very warm, especially during the summer months.

Figure 3C:
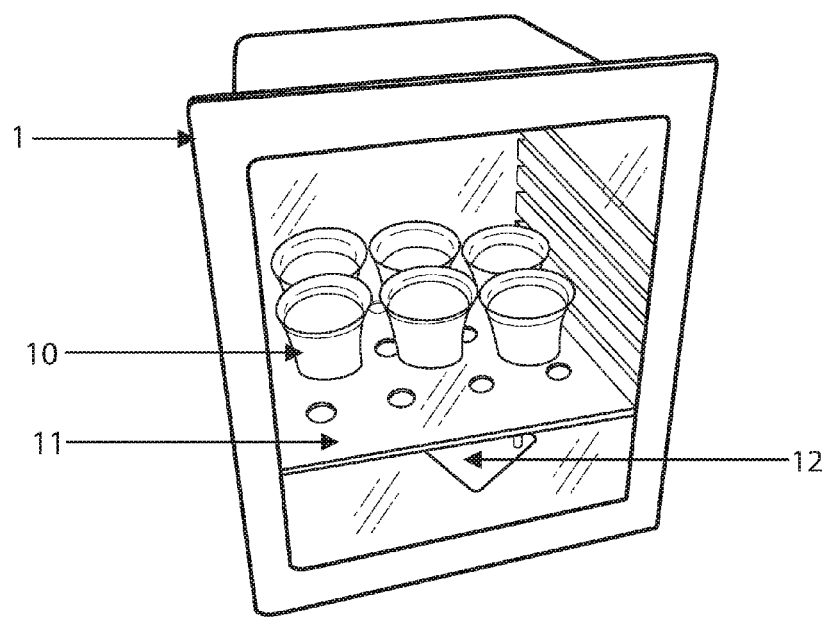
FIG. 3C shows the fumigation chamber that was used for the modeling in FIG. 3A.

The model for FIG. 3A was made as follows: Fumigation was conducted at a laboratory scale with 40 g to 400 g of psyllium husk in a 1 ft$^3$ fumigation chamber. FIG. 3C shows fumigation chamber 1. Psyllium husk samples 10 were placed inside fumigation chamber 1 on perforated floor 11 and below perforated floor 11 is circulating fan 12. The humidity was controlled either by placing a saturated salt solution within the chamber below the floor or pre-equilibrating the samples for a few days in a sealed chamber with a saturated salt solution. Then, a sample population of live insects was sealed in a vial and place below the floor. Two replicate chambers were placed into a constant temperature chamber for the prescribed period of time for the fumigation exposure. Once the prescribed time elapsed, the chamber door was opened to off gas, then the samples were removed for testing and insect mortality was confirmed. Samples were fumigated for 3 hours, 12 hours, or 24 hours. Since the chamber is small, in comparison to the large scale fumigation, off gassing only takes a couple of minutes and can be done by opening the chamber door.

Samples of the psyllium husk were tested for amount of residual inorganic bromide as described herein. The results were analyzed and a kinetic model was determined and is shown in the following expression.

$$\text{Residue} = t \ast e^A \ast e^{B/T(K)} \ast e^{E \ast \text{Pre EQ \% RH}} \ast e^{D \ast \text{Conc.}} \ast e^{\{C \ast t + F \ast G\}}$$

$$\text{Residue} = t \ast e^{14.65745} \ast e^{-4192.224/T(K)} \ast e^{0.3579591 \ast \text{Pre EQ \% RH}} \ast e^{2.7264e-05 \ast \text{Conc.}} \ast e^{\{-0.042662 \ast t + 2.7364e-06 \ast (\text{Conc.}-11055.5) \ast (t-13.4545)\}}$$

Assuming t=24 hours and Conc.=600 mg/kg this expression was used to predict a seasonal variation in residue based on climate weather data from Ahmedabad, India. An estimate of individual sample variation was made using a 46% relative standard deviation (RSD) based on the model root mean square error (RMSE) of 0.399945 compared to the mean response of 0.869657 or about 46% (0.399945/0.869657) and a +3 sigma and +2 sigma estimate was made.

Example 4

Figure 4A:
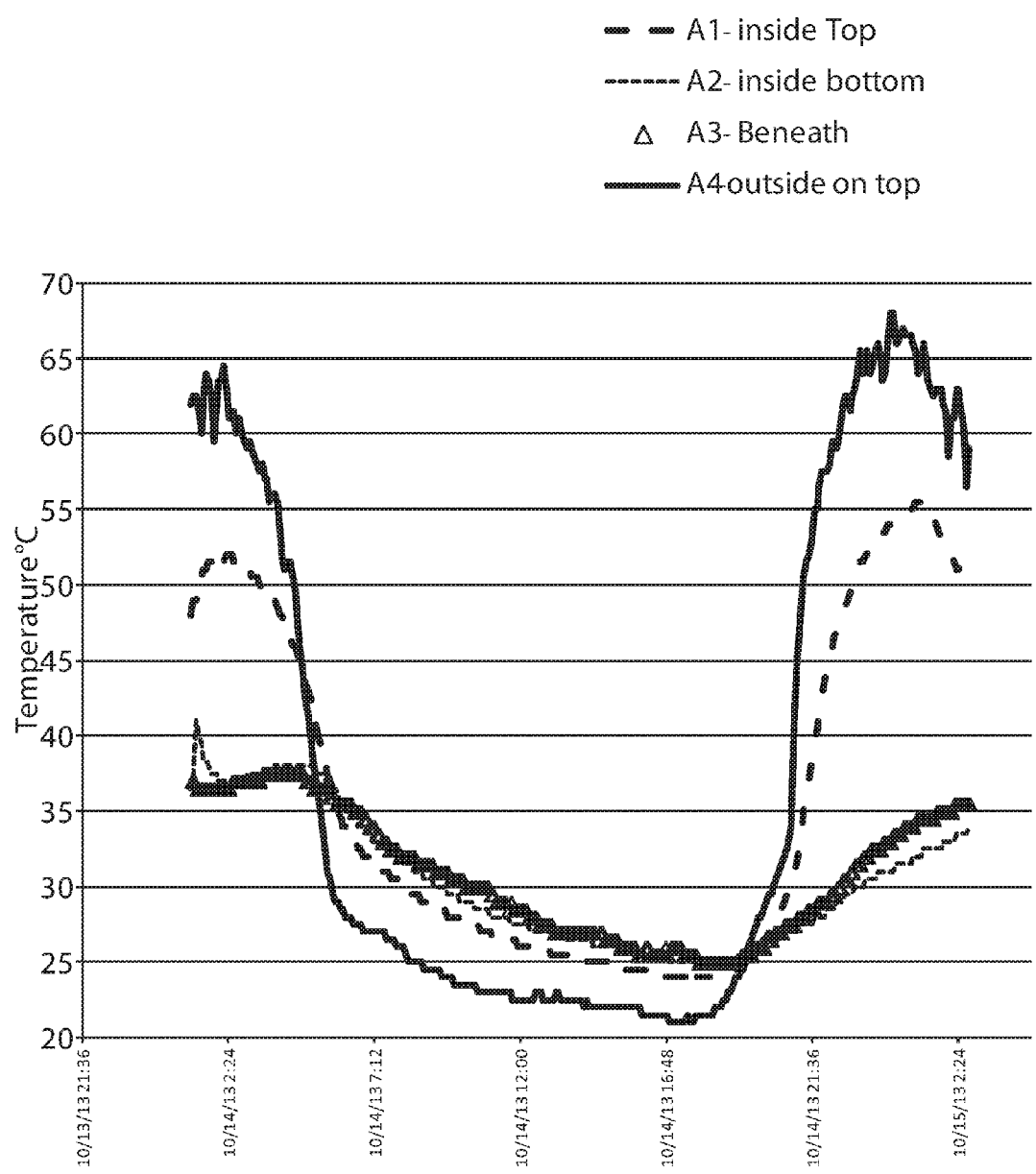
FIG. 4A shows the temperature profile over time for an unsheltered shipping container during fumigation and off gassing.

FIGS. 4A and 4B show the temperature of different portions of the container over a period of about two days during fumigation and off gassing. Temperature data-loggers were placed on top of the container, inside the container on the top to get a representation of the ambient temperature within the container, within the container below the gas inlet port, and beneath the psyllium sacks. The fumigation was started between 23:00 MDT (Mountain Time Zone) on Oct. 13, 2013 and 01:10 MDT. The fumigation ended and the off gassing began between 11:30 MDT on Oct. 14, 2013 and 01:17 MDT on Oct. 15, 2013 and continued for 32 to 77 minutes. FIG. 4A shows the temperature profile for an unsheltered shipping container, Container A. FIG. 4B shows the temperature profile for three sheltered shipping containers, Container B, C, and D.

Table 2, below, shows the mean kinetic temperature of the different portions of the shipping containers.

TABLE 2

| Container | Unsheltered Temperature (° C.) | Sheltered Temperature (° C.) | | |
|---|---|---|---|---|
| | A | B | C | D |
| Outside on top | 50.8 | 42.8 | 43.2 | 43.1 |
| Inside on top | 42.2 | 33.1 | 33.0 | 32.4 |
| Below the gas inlet port | 31.4 | 29.8 | 29.2 | 29.3 |
| Beneath the psyllium sacks | 31.8 | 29.7 | 29.2 | 28.6 |

The sheltered containers resulted in an approximately 9° C. decrease inside the container on the top, which represents the ambient temperature, based on the mean kinetic temperature summarized in Table 2. The sheltered container also resulted in an approximately 9° C. decrease outside but on top of the container. However, there was not a significant difference in temperature between the temperature beneath the container and inside on the bottom of the container.

Sheltering the fumigation chamber, which can be a shipping container, can result in less residue due to the reduced temperatures inside the fumigation chamber. In some examples, the fumigation can occur when the air temperature is warmer. In one example, the psyllium husk fumigation occurs at a temperature of less than or equal to about 35° C., in another example less than or equal to about 39° C., in another example less than or equal to about 41° C., in another example less than or equal to about 43° C., in another example less than or equal to about 46° C., in another example less than or equal to about 48° C., and in another example less than or equal to about 51° C.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, 10."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for fumigating psyllium comprising:
   a. separating psyllium husk from psyllium seed and placing the psyllium husk in bags;
   b. filling a fumigation chamber with the bags of psyllium husk such that the chamber is at least 35% filled by volume with the bags of psyllium husk;
   c. fumigating the psyllium husk with at least about 40 g/m$^3$ of methyl bromide for at least 24 hours;
   d. degassing the chamber for at least about 6 hours to form fumigated psyllium husk;
   wherein the fumigated psyllium husk comprises less than about 50 ppm inorganic bromide residue and wherein the fumigated psyllium husk does not comprise an insect infestation.

2. The method of claim 1 further comprising steam sanitizing the fumigated psyllium husk.

3. The method of claim 1 further comprising removing the fumigated psyllium husk from the fumigation chamber; fumigating a shipping container and putting the fumigated psyllium husk in the shipping container.

4. The method of claim 1 wherein the fumigation chamber comprises from about 50 to about 70 kg psyllium husk per m$^3$ of the chamber.

5. The method of claim 1 wherein the fumigation chamber comprises about 7000 k g to about 12,000 kg psyllium husk.

6. The method of claim 1 wherein the fumigation chamber comprises about 15,000 kg to about 25,000 kg psyllium husk.

7. The method of claim 1 wherein the fumigation chamber is a shipping container.

8. The method of claim 1 wherein the fumigation is performed at a temperature that is less than or equal to about 45° C.

9. The method of claim 1 wherein the fumigation is performed at a temperature that is less than or equal to about 40° C.

10. The method of claim 1 wherein the bags are jute bags.

* * * * *